United States Patent [19]
Hanson

[11] Patent Number: 5,191,787
[45] Date of Patent: Mar. 9, 1993

[54] SOIL ERODIBILITY TESTING

[75] Inventor: Gregory J. Hanson, Stillwater, Okla.

[73] Assignee: The United States of America as represented by the Secretary of Agriculture, Washington, D.C.

[21] Appl. No.: 507,440

[22] Filed: Apr. 11, 1990

[51] Int. Cl.[5] .......................................... G01N 17/00
[52] U.S. Cl. ..................................................... 73/86
[58] Field of Search ..................... 73/78, 84, 86, 865.5, 73/866, 61.4, 784

[56] References Cited

FOREIGN PATENT DOCUMENTS 1099857 6/1984 U.S.S.R. ................................. 73/86
2221762 2/1990 United Kingdom ................... 73/86

OTHER PUBLICATIONS

Hollick, M., 1976, "Towards a Routine Test for the ..." Trans ASAE, 19(6): pp. 1076–1081.

Hanson, Gregory J., 1988, "Large Scale Testing of Soil Erodibility", Southwest Reg Meeting, ASAE, Lubbock, TX, Apr. 14–15, Paper No. SWR-88-101, 12 pages.

Beltaos, S. et al, Oct. 1974, "Impinging Circular Turbulent ..." Proc. ASCE, J. Hyd. Div., 101 (HY 10):1313–1328.

Moore, W. L. et al, "Experiments on the Scour ..." J. of Geophysical Res., vol. 67, No. 4, Apr. 1962, pp. 1437–1446.

Dunn, Irving S., "Tractive Resistance of Cohesive Channels", Jun. 1959, Proc. ASCE, J. Soil Mech and Foundn. Div. 85 (SM3):1–24.

ASCE, 1968, Task Committee on Erosion of Cohesive Materials—Erosion of Cohesive Sediments, Proc. ASCE, J. Hyd. Dir., 94(HY4):1017–1049.

Primary Examiner—Robert Raevis
Attorney, Agent, or Firm—M. Howard Silverstein; John D. Fado

[57] ABSTRACT

The present invention is drawn to soil erodibility testing utilizing: an outer backwater tank, which during testing is filled with water; an inner liner positioned at least partially within the outer backwater tank for minimizing return turbulence and providing a mount for either a feed tube or pin profiler means, and; a feed tube having a nozzle thereon, which is positioned within the interior of the inner liner. Water is forced through the feed tubed and nozzle, into contact with soil to be tested, so that at least a portion of the soil is removed by erosion. The volume of soil removed by erosion is determined based on the differences between an initial soil profile and an eroded soil profile, which may be measured with a pin profiler means.

8 Claims, 4 Drawing Sheets

SOIL ERODIBILITY TESTING

FIELD OF THE INVENTION

The present invention is drawn to a process and apparatus for testing soil erodibility.

BACKGROUND

Water flowing in natural or artificial channels exerts a force on the channel bed in the direction of flow. This force is known as the tractive stress and is dependent on the unit weight of water, depth of water, and the energy slope. This force has the ability to erode or scour an unlined channel bed. The typical equation for modeling erosion in open channel flow is expressed:

$$E_r = K(T_e - T_c) \quad [1]$$

where
- $E_r$ = the erosion rate in volume of soil per unit time per unit area
- $T_e$ = the local effective stress
- $T_c$ = the critical stress
- $K$ = a constant of proportionality, (soil erodibility factor)

In high stress applications, the critical tractive stress is small in comparison to the effective stress, and the equation essentially can be expressed as:

$$E_r = K(T_e) \quad [2]$$

The effective stress is the stress at the soil-water interface causing detachment. As the effective stress is increased in the channel, the rate of erosion is increased by a factor of K. Defining the erodibility, K, is therefore necessary in determining the erosion rate for the stresses anticipated for design conditions.

A report by the American Society of Civil Engineers (ASCE) task committee on Erosion of Cohesive Materials (ASCE, 1968) drew three conclusions related to small apparatus for the purposes of determining soil resistance properties to erosion: (1) Much progress had been made on apparatus to simulate erosion forces; (2) Problems still existed in translating the results to design criteria, and; (3) Simple devices that allowed soil conditions to be easily controlled, or undisturbed samples to be tested, need to be further developed. An assessment of different types of test apparatus is discussed by Hollick, M. 1976 "Towards a routine test for the assessment of critical tractive forces of cohesive soils", Trans. of the ASAE, 19(6):1076–1081. Many of the devices have been developed to assess the critical tractive stress.

SUMMARY OF THE INVENTION

The present invention is drawn to a highly advantageous and novel apparatus and process with which the aforementioned soil erodibility factor may be determined, for any of a wide variety of soils and under a wide variety of conditions. Said factor may then be utilized in the above equations to predict erosion rate. Measurement of erodibility and prediction of erosion rate are clearly of extensive utility in many engineering applications, such as design and construction of canals, roads, dams, embankments, earth auxiliary spillways, ditches (e.g. roadside ditches), rill erosion determinations, agricultural land management, land reclamation e.g. mining reclamation activities, etc.

Therefore, it is a first object of the present invention to provide accurate determination of soil erodibility either: (1) in-situ (i.e. testing the soil in place where it naturally occurs) thus providing the advantages of, (a) allowing less disturbance to the soil prior to testing, and (b) permitting the operator to use water from the local area as the testing fluid (it has been found that water chemistry may be important in defining the soil erodibility), or; (2) in a laboratory type setting.

It is another object of the instant invention to permit accurate measurement of soil erodibility, which measurement may be utilized in a plurality of design and engineering applications.

Another object of the present invention is to provide such erodibility measurement utilizing a process which is easy to carry out, requires a reasonably small amount of water and employs a measurement device which is portable.

Other objects and advantages of the instant invention will become readily apparent from the ensuing description.

DESCRIPTION OF THE PREFERRED EMBODIMENTS

Figure 1:
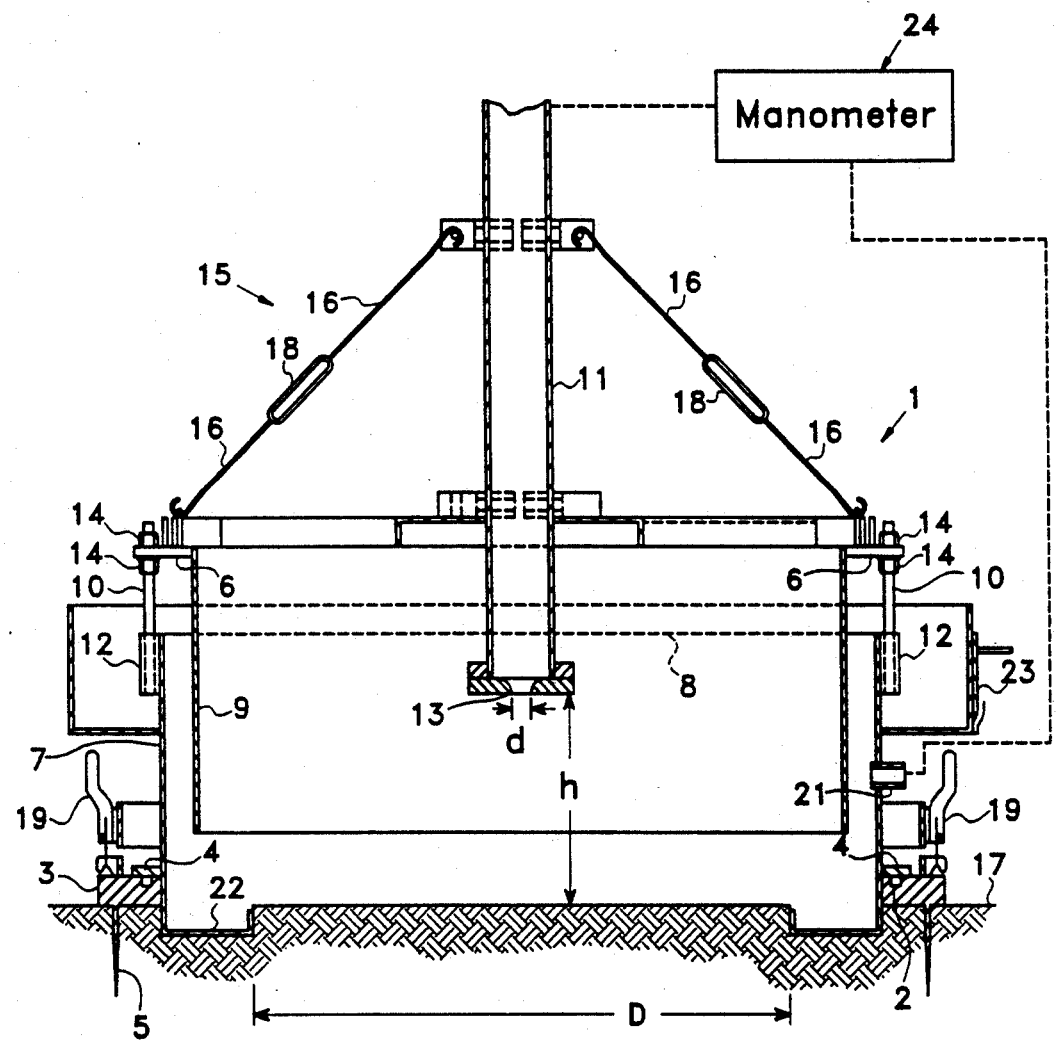
FIG. 1 is a side view of a cross-section of a device of the present invention, with a feed tube and nozzle positioned therein

FIG. 1 illustrates a vertical submerged jet apparatus of the present invention, generally designated 1, of a type which may be taken to the field to determine soil erodibility. The apparatus 1 includes a backwater tank 7 which may be of any convenient configuration, such as cylindrical or polygonal. The tank 7 may be fabricated from any convenient, rigid, durable material such as steel, aluminum, or plastic. The tank 7 is held by any convenient quick release means, such as quick release clamps 19, to a base ring 3 having thereon a sealing ring 5. The sealing ring 5 is driven into the soil until the base ring 3 is in contact with the ground, to form a water tight seal with the ground. The base ring 3 and sealing ring 5 are collectively referred to as the foundation ring means. Optionally, seal ring 4 may be connected to the exterior of tank 7 and pulled by quick release clamps 19 against a gasket 2 in the top of base ring 3. The tank 7 defines a first aperture at an upper portion thereof, for egress of water from said aperture. In the embodiment illustrated in FIG. 1 the tank 7 defines the first aperture at its upper terminus (designated 8) i.e. the tank 7 is open at its top, therefore water may egress over the upper most edge of the tank and spill over into a discharge through 23. Thus the tank 7 acts as a weir i.e. when water is directed into tank 7, the water level will be up to the level designated by the numeral 8 in FIG. 1, whereby both the lower extremity of feed tube 11 and the nozzle 13 will be submerged in the water. The backwater tank 7 also defines a second aperture at a lower portion thereof, through which soil to be tested may be exposed to the interior of the backwater tank. The foundation ring means is sealed to the lower portion of the outer backwater tank for providing an essentially water tight seal between, the portion of the tank defining the second aperture and the soil to be tested. In the embodiment shown in FIG. 1 the inner liner defines the second aperture at its lower terminus i.e. the inner liner has an open bottom. For a cylindrical backwater tank, the diameter of soil surface exposed to the interior of the backwater tank (designated "D" in FIG. 1) may range from as large as may be convenient to about 0.3 meters, is preferably from about 0.6 meters to about 0.3 meters, and most preferably is about 0.46 meters. A device of the present invention which is intended to be portable, will typically be of dimensions such that the inside diameter of a backwater tank which is cylindrical will range from about 0.4 meter to about 1 meter. An inner liner 9 is provided to: (1) act as a baffle to minimize return turbulence to the jet; (2) the upper surface of the inner liner 9 may act as a mount for the feed tube, and; (3) the inner liner may also act as a mount for the pin profiler means used to determine material loss. The inner liner is positioned at least partially within the outer backwater tank, and defines a first aperture at an upper portion thereof through which the feed tube 11 extends. The inner liner also defines a second aperture at a lower portion thereof, through which soil to be tested may be exposed to the interior of the inner liner. In the embodiment shown in FIG. 1 and 2 the inner liner defines said second aperture at the lower terminus thereof i.e. the bottom of the inner liner is open. The inner liner may be of any convenient overall configuration, such as cylindrical or polygonal. The inner liner may be fabricated from any convenient, rigid, durable material such as steel, aluminum, or plastic. The inner liner may be held level by any convenient adjustable mounting means for permitting the position of said inner liner to be adjusted relative to the outer backwater tank (i.e. so that the inner liner may be leveled even if the outer tank is not level). Such adjustable mounting means may for example take the form of threaded rods 10 each of which, extends through an internally screw threaded fitting 12 on the outer backwater tank 7, and is held by a pair of nuts 14 to a support ring 6 attached to the upper periphery of inner liner 9. A feed tube 11 extends through the top of the inner liner, and has its lower terminus positioned within the interior of the inner liner. The feed tube may for example be constructed of steel, polyvinyl chloride or preferably from PLEXIGLAS ™. The diameter of the feed tube may for example range from, as large as is convenient to about 40 millimeters, preferably from about 100 millimeters to about 40 millimeters, and most preferably is about 51 millimeters. In use, the feed tube 11 is connected to a source of water, such as a constant head tank. The feed tube may conveniently be held by a jet hanger generally designated in FIG. 1 by the numeral 15. The jet hanger 15 may include rods 16 and turnbuckles 18. A nozzle 13 is connected to the lower terminus of feed tube 11. The nozzle 13 must define a circular aperture having a rounded entrance (e.g. as illustrated in FIG. 1), and the nozzle must define an exit diameter d of about 13 mm. The tube 11 is shown at a height h from the ground level 17. Height h must be about 0.22 meters. Also, the nozzle must be lower than the first aperture of the outer backwater tank so that when the backwater tank is filled with water the nozzle will be submerged. A pipe coupling 21 is connected to a conventional manometer 24 which is also connected to feed tube 11, so that the pressure differential between the feed tube and the interior of the outer backwater tank may be measured. Optionally, a trough configured to accept the lower terminus of the backwater tank may be formed in the soil, and a tank settling trough 22 may be placed in the trench. The trench and trough 22 serve two purposes: (1) to act as an area that soil can settle into and be cleaned from as necessary, and; (2) to protect the soil surface during backfilling of the tank.

A soil is tested by first preparing a site. The site is leveled and flattened. Forms are placed on the soil surface for the purposes of cutting a trench. A soil planer is used to cut a trench for the tank settling trough 22. After the trench is formed, it is filled with an insert (which may for example be made of plywood) and the site is properly wetted to saturate the soil. When the site is ready for testing, a lower portion of the foundation ring means (e.g. the sealing ring) is inserted into the soil (along the outside edge(s) of the precut trench) to an extent that an upper portion of the foundation ring means (e.g. base ring 3) seats against the surface of the soil to be tested, so that the foundation ring means and the soil form an essentially water tight seal there between. The backwater tank 7 is then set in place, such that its lower most terminus is inserted into the base ring 3 and settling trough 22 (adjacent to the outer periphery of the trough), and clamped down.

Figure 2:
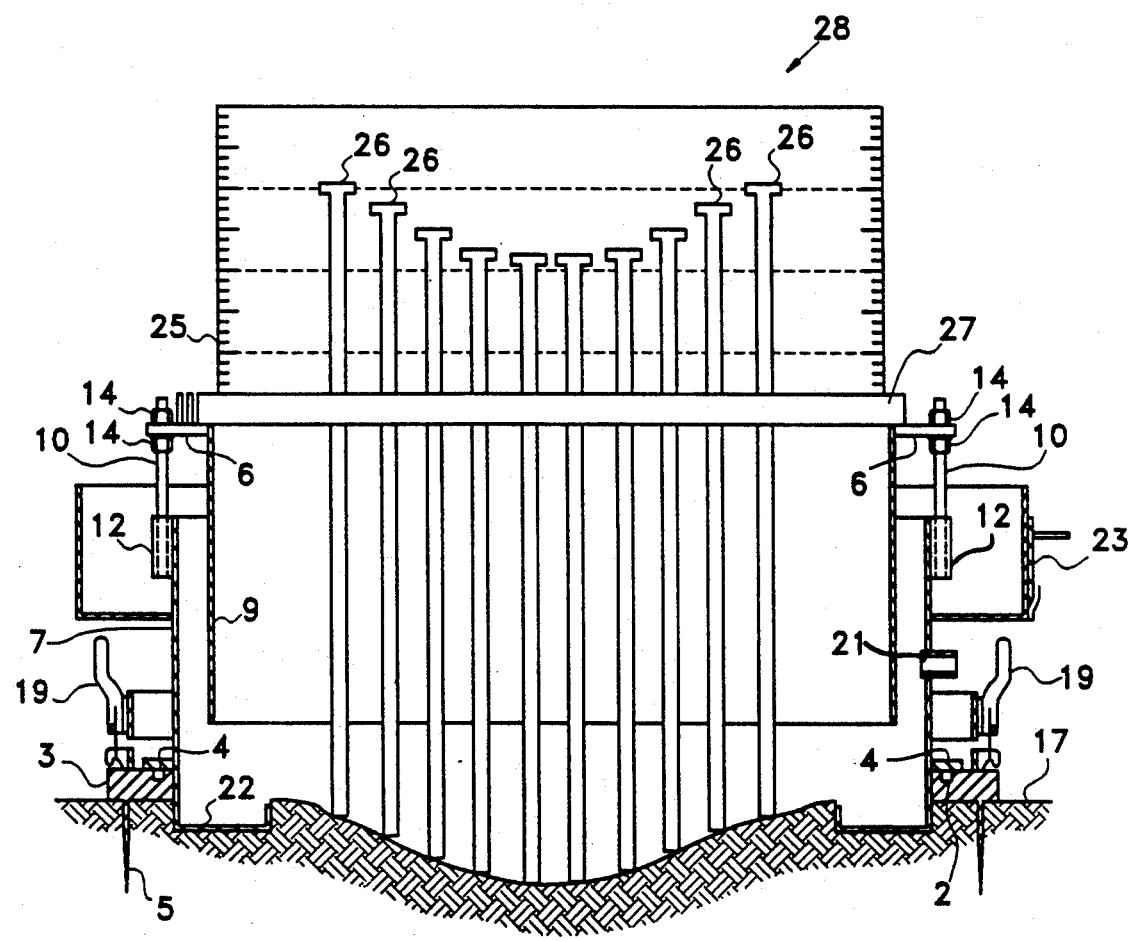
FIG. 2 is a side view of a cross-section of a device of the present invention, with pin profiler means positioned therein.

The inner liner 9 is placed on the leveling bolts 10 of the backwater tank pin profiler means, generally designated by the numeral 25 is placed on the inner liner 9. The pin profiler means includes a plurality of pins 26, and holding means for holding said plurality of pins such that each pin is individually displaceable along its longitudinal center axis. Such holding means may for example take the form of a hanger 27 (such as a bar, board, rail, etc.) defining a plurality of apertures which extend completely through the hanger, with each pin 26 slideably held within one of the apertures. As shown in FIG. 2 at least a portion of each of the pins is positioned within the outer backwater tank 7, proximate to a lower portion of the tank 7, so that each of the pins 26 may contact the soil. The pin profiler means 25 may for example include a linear array of 31 magnesium pins of 3 millimeter diameter and 0.51 meter length, spaced 15 millimeters on center. The relative elevations of the tops of the pins are determined utilizing a background grid 28. The pin profiler means is designed such that it may conveniently be interchanged with the tube and nozzle. An initial pin profile of the soil surface is taken to determine the original soil surface elevation prior to any testing. The pin profiler means is removed and the backwater tank is backfilled with water. This operation is carried out by placing a hose in the discharge trough 23 causing the water to flow over the backwater tank upper terminus in the opposite direction to the direction that the water flows during a jet test run. Subsequent to the step of filling the tank 7 with water, the water may be held in the tank for a period of time sufficient to saturate the soil to be tested prior to forcing water through the feed tube and nozzle. The head on the jet is set, the discharge from the nozzle is closed off, the jet is submerged in the tank, and a run is started. The submerged jet of water produces erosion of the soil in the vicinity of the jet impact area i.e. water forced through the feed tube and nozzle into contact with the soil removes by erosion at least a portion of the soil. The impact of the jet causes pressures and shear stresses at the soil-water interface resulting in the formation of a scour hole directly beneath the jet. A timing sequence of 10, 30, 60, and 100 minute intervals for jetting the soil surface are indicated by the preliminary data. This results in a total jetting time of 200 minutes. Following each time interval a pin profile, taken every 20 degrees, should be recorded to determine volume of soil removed i.e. based on the differences between the initial profile and the eroded profile(s). The pin profiler means may be used without draining the tank. The pins should be kept clean of any buildup of material to assure that they are able to slide properly in their hanger 27. It is preferred that a number of sites be run in this fashion in order to assure repeatability and to assure reasonable estimates of the soil's erodibility.

The following example is intended only to further illustrate the invention and is not intended to limit the scope of the invention which is defined by the claims.

EXAMPLE

The soils identified as A, B, C, and D (Table 1) were placed and compacted in 15.2 meter sections 0.91 meter wide by 0.23 meter deep. The erodibility factor, K (Table 1) was determined from open channel testing similar to the procedures previously reported in G. J. Hanson, 1988, "Erosion rates of two cohesive soils", ASAE Paper No. 88-2127, ASAE, St. Joseph, Mich. 49085-9659, 15 p.

TABLE 1

SUMMARY OF SOIL PARAMETERS

| Soil Parameter | Soil A | Soil B | Soil C | Soil D |
|---|---|---|---|---|
| Liquid limit | 21 | 37 | 26 | — |
| Plastic limit | 17 | 19 | 20 | NP |
| Plasticity index | 4 | 18 | 6 | 0 |
| % Sand >0.05 mm | 57 | 37 | 48 | 67 |
| % Silt >0.002 mm | 27 | 36 | 33 | 26 |
| % Clay <0.002 mm | 16 | 27 | 19 | 7 |
| U.S.C.[1] | CL-ML | CL | CL-ML | SM |
| A.S.C.[2] | sandy loam | clay loam | loam | sandy loam |
| Soil Erodibility factor K (cm/Pa-h) | 0.36 | 0.005 | 0.8–0.002 | 2.77 |

[1]"U.S.C." stands for Unified Soil Classification
[2]"A.S.C." stands for U.S. Department of Agriculture Soil Texture Classification The soils were compacted using a sheepsfoot roller. The average dry densities at the time of testing of the four soil materials are shown in Table 2.

TABLE 2

AVERAGE DRY DENSITY OF SOIL MATERIAL

| SOIL | DRY DENSITY (gm/cc) |
|---|---|
| A | 1.65 |
| B | 1.57 |
| C | 1.61 |
| D | 1.64 |

In utilizing the device of the present example, initially the site was screeded so that it was flat and level. Forms were placed on the soil surface for the purpose of cutting a trench. A soil planner was used to cut a trench for the tank settling trough. After the trench was formed, it was filled with a plywood insert and the site is wetted to saturate the soil.

When the site was ready for testing, the foundation ring means was pushed into the soil along the outer periphery of the precut trench. The backwater tank was then set in place in the base ring and trench and latched down. The cylindrical liner is placed on the leveling bolts of the backwater tank and leveled. A pin profile of the soil surface was taken, determining the original surface elevation prior to any testing. The pin profiler means was removed, and the backwater tank is backfilled with water. After the head on the jet was set and the discharge from the nozzle was closed off, the jet was submerged in the tank, and a run was started. A typical timing sequence of 10, 30, 60, and 100-minute intervals was used to result in total test time of 200 minutes. For more resistant soils 10, 30, 60, 100 and 1000-minute intervals were used. Following each time interval, a pin profile was taken at horizontal angle increments of 20 degrees. Results were recorded to allow calculation of the volume of material removed. The variables involved in such soil erodibility testing are related by a dimensionless equation of the form:

$$\frac{\sqrt[3]{Vol}}{h} = \Phi\left(\frac{h}{d}, \frac{pVd}{u}, \frac{ut}{pd^2}, \frac{uK}{d}\right) \quad [3]$$

where:
Vol = volume of material removed during a jetting event
h = elevation of jet above the soil surface
d = diameter of the jet nozzle
V = jet velocity
t = time
p = mass density of fluid
u = dynamic viscosity of the fluid
K = soil erodibility factor of the soil.

Soil erodibilities of soils A, B and D were determined from large scale open channel testing as described in: G. J. Hanson, 1988, "Large scale testing of soil erodibility", Southwest Region Meeting, Am. Soc. of Ag. Eng., Lubbock, Tex., April 14–15, Paper No. SWR 88-101, 12 pages., and; G. J. Hanson, 1988, "Erosion rates of two cohesive soils", International Summer Meeting of the Am. Soc. of Ag. Eng., Rapid City, S.Dak., June 26–29, Paper No. 88-2127, 15 pages. These same soils were then prepared in similar fashion and tested with an in-situ submerged jet device as shown in instant FIG. 1. The jet height h was maintained at approximately 0.22 meters above the original soil surface, and the jet diameter d was about 13 millimeters. Therefore, the height factor (h/d) can be eliminated from the calibration as long as h and d are held at these specified dimensions. Measurements of soil erodibility by these two different methods were used to calibrate the device of this example. The erodibility of soil C was then determined from the results of this calibration.

Calibration of the submerged jet device was carried out by a comparison of these dimensionless terms versus the scour factor (cube root of vol. divided by the jet height h) on an individual basis. A linear model was used to determine the best-fit relationship to the data obtained with the specific device of the present example. The resulting equation was:

$$\frac{\sqrt[3]{Vol}}{h} = 0.00436\left(\frac{pVd}{u}\right)0.67\left(\frac{ut}{pd^2}\right)0.065\left(\frac{Ku}{d}\right)0.138 \quad [4]$$

Figure 3:
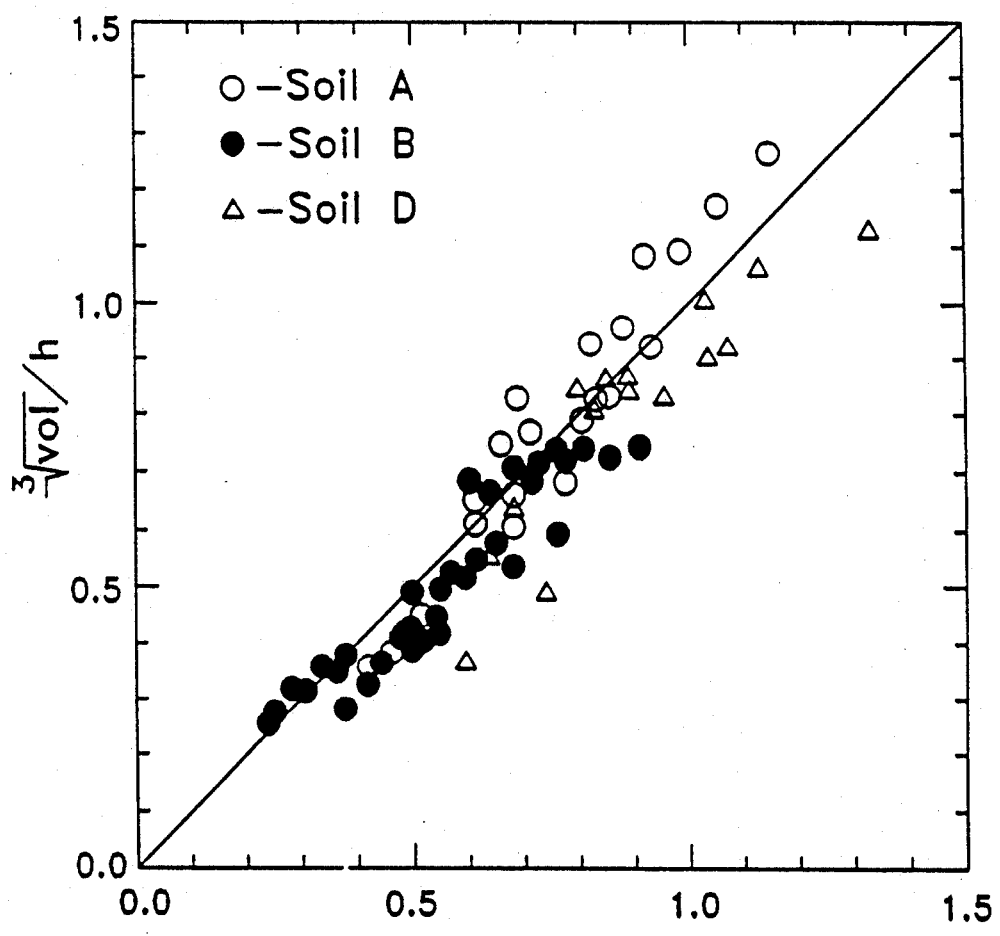
FIG. 3 is a graph of observed scour factor versus predicted scour factor.

FIG. 3 shows the predicted values of the scour factor versus the actual measured values. This plot indicates the accuracy of the device of the present example for estimating the erodibility of other soils.

In order to apply this equation to estimate the erodibility of other soils, the equation must be rearranged such that K becomes the dependent variable since it is unknown and the other factors become the independent variables since they are measured. The equation then has the following form:

$$K = \left( \frac{\sqrt[3]{Vol/h}}{0.00436 \left(\frac{pVd}{u}\right)^{0.67} \left(\frac{ut}{pd^2}\right)^{0.065}} \right) 7.25 \times \frac{d}{u} \quad [5]$$

Figure 4:
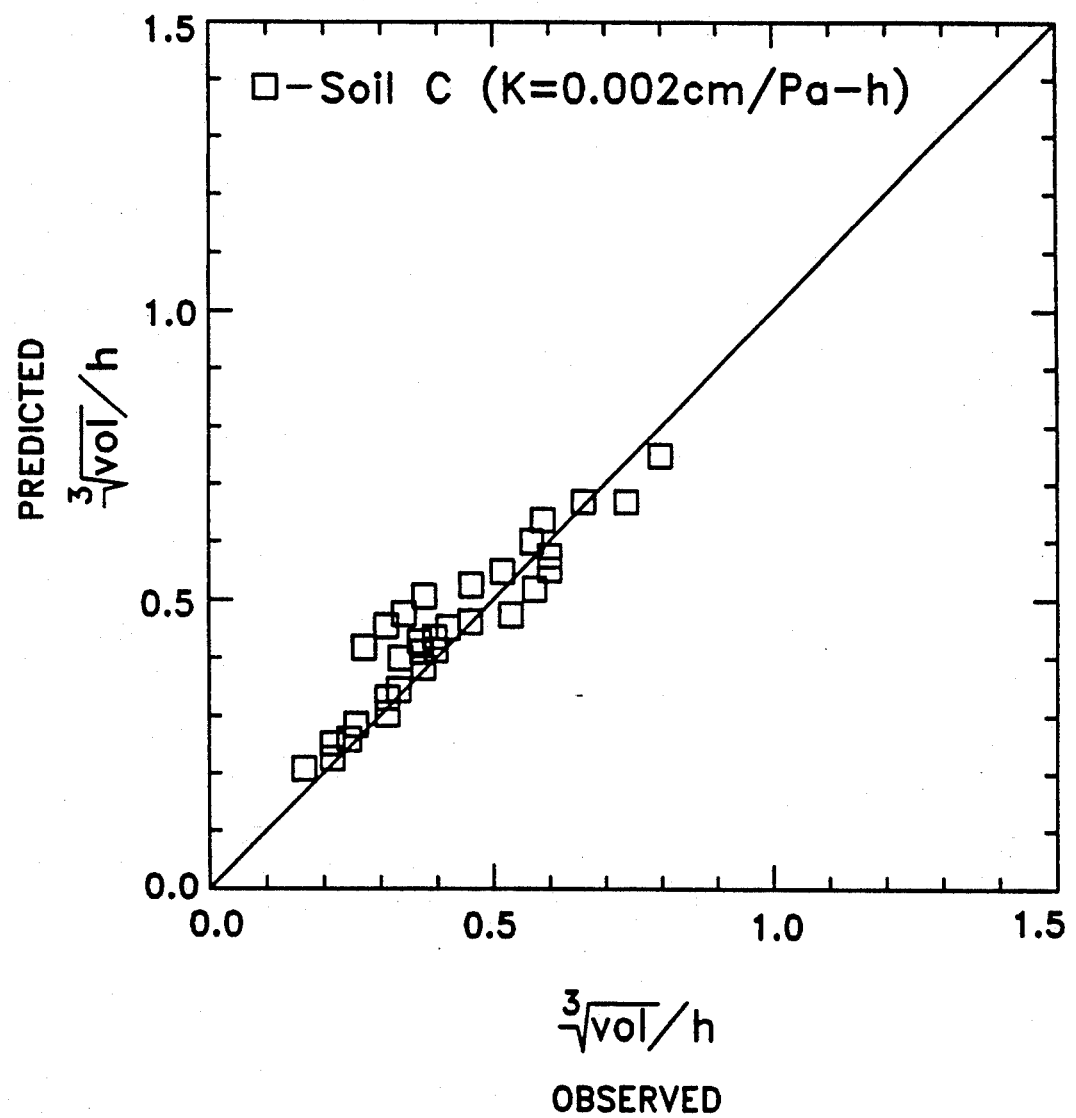
FIG. 4 is a graph of predicted scour factor versus observed scour factor based on K determined from jet test results.

As an application of this technique, the erodibility of soil C was determined. Seven jet sites were tested with 4 to 5 jetting time periods at each site resulting in a total of 33 tests to determine K. The mean value of K determined from the jet test was 0.002 (cm/hr)/Pa with a standard deviation of 0.001. Based on these results, soil C has an average erodibility factor equivalent to that observed in the last 20 hours of testing in the open channel testing (Table 1). The K factor determined from the jet test was substituted into Equation 4 to compare the observed scour factor versus the predicted scour factor (FIG. 4).

The foregoing detailed descriptions and examples are given merely for purposes of illustration. Modifications and variations may be made therein without departing from the spirit and scope of the invention.

INDEX OF APPARATUS ELEMENTS DESIGNATED BY A NUMERAL

| INDEX OF APPARATUS ELEMENTS DESIGNATED BY A NUMERAL |
| --- |
| 1. Vertical submerged jet apparatus |
| 2. Gasket |
| 3. Base ring |
| 4. Seal ring |
| 5. Sealing ring |
| 6. Support ring |
| 7. Outer backwater tank |
| 8. Backwater tank upper terminus |
| 9. Inner liner |
| 10. Threaded rods |
| 11. Feed tube |
| 12. Internally screw threaded fitting |
| 13. Nozzle |
| 14. Nuts |
| 15. Jet hanger |
| 16. Rods |
| 17. Ground Level |
| 18. Turnbuckles |
| 19. Quick release clamps |
| 21. Pipe coupling |
| 22. Tank settling trough |
| 23. Discharge trough |
| 24. Manometer |
| 25. Pin profiler means |
| 26. Pins |
| 27. Hanger |
| 28. Background grid |

I claim:

1. An apparatus comprising:
   an outer backwater tank defining a first aperture at an upper portion thereof for egress of water, said outer backwater tank also defining a second aperture at a lower portion thereof through which soil to be tested may be exposed to the interior of said tank;
   an inner liner positioned at least partially within said outer backwater tank, said inner liner defining a first aperture at an upper portion thereof through which a feed tube extends, said inner liner also defining a second aperture in a lower portion thereof through which soil to be tested may be exposed to the interior of said inner liner;
   said feed tube having a lower terminus positioned within the interior of said inner liner, said feed tube having at said lower terminus thereof a nozzle, said nozzle defining a circular aperture having a rounded nozzle entrance and a nozzle exit diameter of about 13 millimeters;
   said nozzle being positioned within the interior of said inner liner such that said nozzle will be about 0.22 meters from said soil to be tested and said nozzle is lower than said first aperture of said outer backwater tank, whereby when said outer backwater tank is filled with water said nozzle will be submerged, and;
   foundation ring means sealed to said lower portion of said outer backwater tank for providing an essentially water tight seal between said lower portion of said outer backwater tank defining said second aperture and said soil to be tested.

2. The apparatus of claim 1 wherein said outer backwater tank and said inner liner are cylindrical.

3. The apparatus of claim 2 wherein said outer backwater tank defines an inner diameter from about 0.4 meter to about 1 meter.

4. The apparatus of claim 1 wherein said inner liner is connected to said outer backwater tank by adjustable mounting means for permitting the position of said inner liner to be adjusted relative to said outer backwater tank.

5. The apparatus of claim 4 wherein said adjustable mounting means includes threaded rods.

6. The apparatus of claim 1 wherein said foundation ring means is connected to said outer backwater tank by quick release clamps.

7. The apparatus of claim 1 wherein said feed tube is connected to a source of water.

8. The apparatus of claim 1 wherein said feed tube and the interior of said outer backwater tank are both connected to a manometer.

* * * * *